United States Patent [19]

Karanewsky

[11] Patent Number: 4,598,071
[45] Date of Patent: Jul. 1, 1986

[54] CERTAIN 3-PHOSPHINYL-AMINO-2-OXO-1H-AZOCINE OR AZONINE-1-ACETIC ACID DERIVATIVES HAVING ANTI-HYPERTENSIVE PROPERTIES

[75] Inventor: Donald S. Karanewsky, East Windsor, N.J.

[73] Assignee: E. R. Squibb & Sons, Inc., Princeton, N.J.

[21] Appl. No.: 675,913

[22] Filed: Nov. 28, 1984

Related U.S. Application Data

[62] Division of Ser. No. 479,429, Mar. 28, 1983, Pat. No. 4,533,661.

[51] Int. Cl.$^4$ .................. C07F 9/65; A61K 31/395
[52] U.S. Cl. ........................... 514/79; 514/89; 514/91; 546/24; 549/6; 260/239 B
[58] Field of Search ............ 260/239 B; 546/24; 514/183, 79, 91; 549/6

[56] References Cited

U.S. PATENT DOCUMENTS 4,379,146  4/1983  Greenlee et al. .................. 514/7
4,409,146  10/1983 Thorsett et al. ............ 260/239.3 R
4,432,971  2/1984  Karanewsky et al. ............... 514/80

FOREIGN PATENT DOCUMENTS 0046289  2/1982  European Pat. Off. ..... 260/239.3 R
0046291  2/1982  European Pat. Off. ..... 260/239.3 R
0046292  2/1982  European Pat. Off. ..... 260/239.3 R

OTHER PUBLICATIONS

Brenner et al., "Eine Einbache Synthese von L-Lysin", Helv. Chem. Acta, vol. 41, pp. 181-188 (1958).
Blicke et al., "The Preparation of Basic Alcohols . . . ", J. Am. Chem. Soc., vol. 76, pp. 2317-2322 (1954).
Wilson et al., "Stereochemistry, Conformational Analysis . . . ", J. Org. Chem., vol. 44, pp. 330-336 (1979).
Nagasawa et al., "Medium Ring Homologs of Proline . . . ", J. Med. Chem., vol. 14, pp. 501-508 (1971).

Primary Examiner—Alan L. Rotman
Attorney, Agent, or Firm—Lawrence S. Levinson; Stephen B. Davis

[57] ABSTRACT

Phosphonamide substituted lactams of the formula

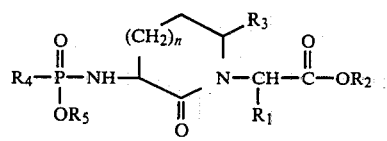

are disclosed. These compounds are useful as hypotensive agents.

9 Claims, No Drawings

CERTAIN 3-PHOSPHINYL-AMINO-2-OXO-1H-AZOCINE OR AZONINE-1-ACETIC ACID DERIVATIVES HAVING ANTI-HYPERTENSIVE PROPERTIES

BACKGROUND OF THE INVENTION

This is a division of application Ser. No. 479,429, filed Mar. 28, 1983, now U.S. Pat. No. 4,533,661.

Greenlee et al. in European Patent Application No. 58,427 disclose that phosphonamide derivatives of proline, pipecolic acid, and thiazolidinecarboxylic acid possess angiotensin converting enzyme inhibition activity.

Harris et al. in European Patent Application No. 46,289 disclose that various substituted enantholactam derivatives possess angiotensin converting enzyme inhibition activity.

Harris et al. in European Patent Application No. 46,291 disclose that various substituted caprolactam derivatives possess angiotensin converting enzyme inhibition activity.

Harris et al. in European Patent Application No. 46,292 disclose that various substituted caprylolactam derivatives possess angiotensin converting enzyme inhibition activity.

SUMMARY OF THE INVENTION

This invention is directed to the lactam compounds of formula I and salts thereof

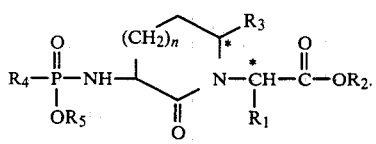

n is an integer from 1 to 4.

$R_1$ is hydrogen, lower alkyl, amino substituted lower alkyl, hydroxy substituted lower alkyl, or halo substituted lower alkyl.

$R_3$ is hydrogen, lower alkyl,

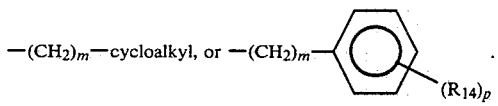

m is zero or an integer from 1 to 4.

$R_{14}$ is hydrogen, lower alkyl of 1 to 4 carbons, lower alkoxy of 1 to 4 carbons, lower alkylthio of 1 to 4 carbons, halo, trifluoromethyl, or hydroxy.

p is an integer from 1 to 3 provided that p is more than one only if $R_{14}$ is hydrogen, methyl, methoxy, chloro, or fluoro.

$R_4$ is alkyl of 1 to 10 carbons,

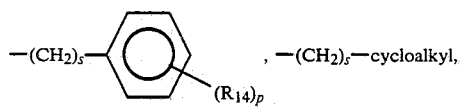

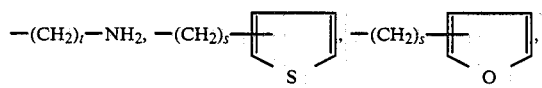

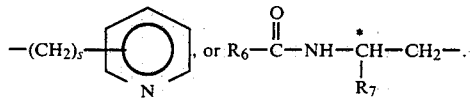

s is zero or an integer from 1 to 7.

t is an integer from 1 to 8.

$R_6$ and $R_7$ are independently selected from lower alkyl, halo substituted lower alkyl,

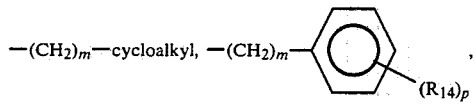

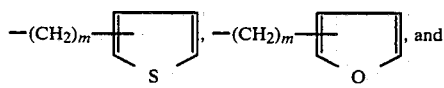

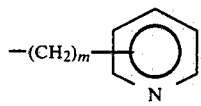

$R_5$ and $R_2$ are independently selected from hydrogen, lower alkyl, benzyl, benzhydryl, salt forming ion, or

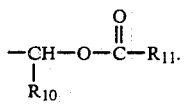

$R_{10}$ is hydrogen, lower alkyl, cycloalkyl, or phenyl.

$R_{11}$ is hydrogen, lower alkyl, lower alkoxy, cycloalkyl, phenyl, benzyl, or phenethyl.

DETAILED DESCRIPTION OF THE INVENTION

This invention in its broadest aspects relates to the lactam compounds of formula I above, to compositions containing such compounds and to the method of using such compounds as anti-hypertensive agents.

The term alkyl used in defining $R_4$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo, and fluoro.

The term halo substituted lower alkyl refers to such lower alkyl groups described above in which one or more hydrogens have been replaced by chloro, bromo, or fluoro groups such as trifluoromethyl, which is preferred, pentafluoroethyl, 2,2,2-trichloroethyl, chloromethyl, bromomethyl, etc. Similarly, the terms amino substituted lower alkyl and hydroxy substituted lower alkyl refer to such lower alkyl groups described above in which one or more hydrogens have been replaced by —NH₂ or —OH, i.e., aminomethyl, 2-aminoethyl, 3-hydroxypropyl, etc.

The symbols

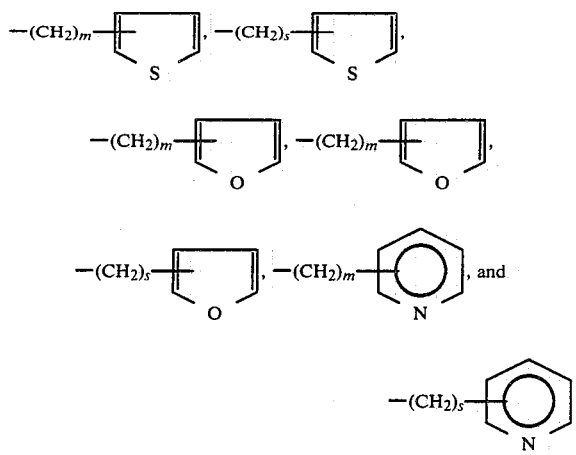

represent that the alkylene bridge is attached to an available carbon atom.

The compounds of formula I wherein R₄ is alkyl,

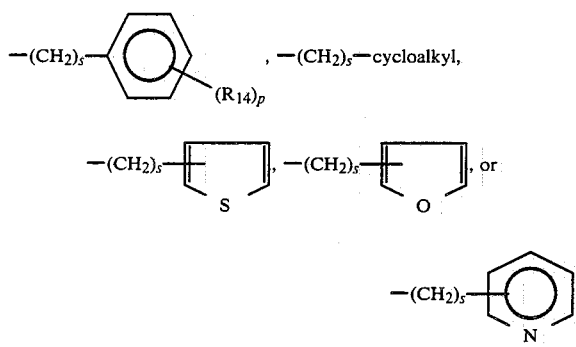

are prepared by coupling a phosphonochloridate of formula II wherein R₅ is lower alkyl, benzyl or benzhydryl

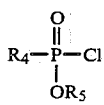 (II)

with the lactam ester of the formula

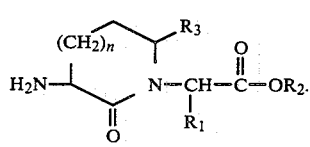 (III)

Preferably, the lactam ester of formula III is in its hydrochloride salt form and R₂ is lower alkyl, benzyl, or benzhydryl.

The products of formula I wherein either or both of R₅ and R₂ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein R₅ and R₂ are hydrogen.

The ester products of formula I wherein R₂ is

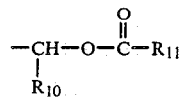

may be obtained by employing the lactam of formula III in the above reaction with the ester group already in place.

The ester products of formula I wherein R₂ is

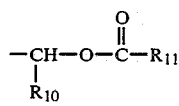

can also be obtained by treating the product of formula I wherein R₂ is hydrogen with a molar equivalent of the compound of the formula

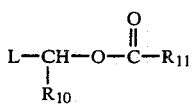 (IV)

wherein L is a leaving group such as chlorine, bromine, tolylsulfonyloxy, etc. The diester products wherein R₅ and R₂ are the same and are

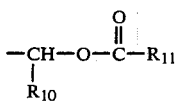

can be obtained by treating the product of formula I wherein R₅ and R₂ are both hydrogen or an alkali metal salt with two or more equivalents of the compound of formula IV.

The ester products of formula I wherein R₅ is

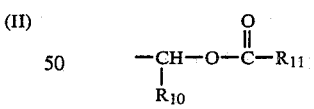

can be obtained by treating the product of formula I wherein R₅ is hydrogen or an alkali metal salt and R₂ is benzyl or benzhydryl with the compound of formula IV in the presence of base. Removal of the R₂ ester group such as by hydrogenation yields the products of formula I wherein R₅ is

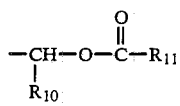

and R₂ is hydrogen.

The phosphonochloridates of formula II are described in the literature and in particular by Kosolapoff et al. in Organic Phosphorous Compounds, Vol. 7, Chapter 18 (Wiley, 1972).

The compounds of formula I wherein $R_4$ is —(CH$_2$)$_r$—NH$_2$ are prepared by reacting a phthalidyl protected compound of the formula

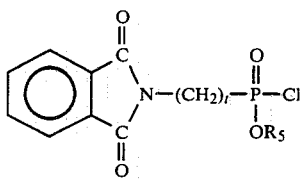
(V)

wherein $R_5$ is lower alkyl, benzyl or benzhydryl with the lactam ester of formula III, preferably wherein $R_2$ is benzyl, in the presence of triethylamine to yield the protected compound of the formula

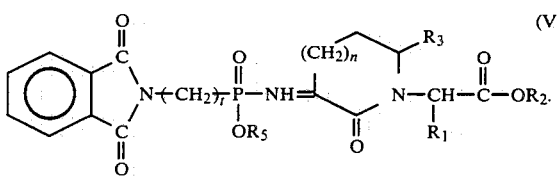
(VI)

Treatment with hydrazine removes the phthalidyl protecting group after which the $R_5$ and $R_2$ ester group can be removed as described previously to yield the corresponding diacid compounds of formula I.

The phosphonochloridates of formula V can be prepared by treating a phthalidyl protected alkylbromide of the formula

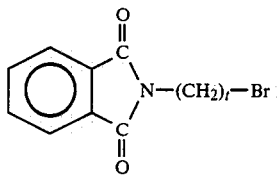
(VII)

with a trialkylphosphite of the formula

 (VIII)

to yield the diester of the formula

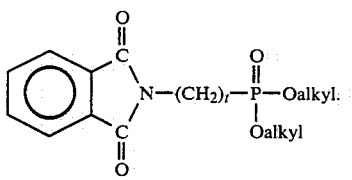
(IX)

Treatment of this diester with trimethylsilylbromide yields the phosphonic acid of the formula

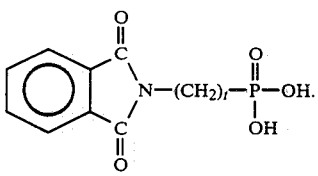
(X)

The acid of formula X can then be treated with phosphorus pentachloride and an alcohol of the formula $R_5$—OH    (XI)

in the presence of triethylamine to give the compound of formula V.

The compounds of formula I wherein $R_4$ is

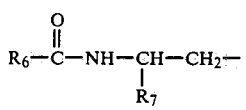

are prepared as follows. A protected amine of the formula

Ts—NH—CH(R$_7$)—CH$_2$—O—Ts    (XII)

wherein Ts is tolylsulfonyl, i.e.,

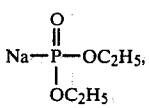

is reacted with sodium diethyl phosphonate, i.e.,

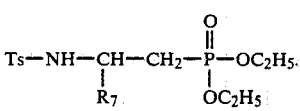

to yield the intermediate of the formula

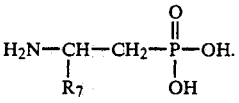
(XIII)

Treatment with hydrogen bromide (48%) in the presence of phenol with heat yields the aminophosphonic acid of the formula

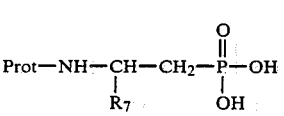
(XIV)

The aminophosphonic acid of formula XIV is then reacted with benzyloxycarbonyl chloride or phthalic anhydride to yield Prot—NH—CH(R$_7$)—CH$_2$—P(=O)(OH)—OH    (XV)

wherein Prot is benzyloxycarbonyl or phthalidyl. The acid of formula XV is then converted to the phosphonochloridate of the formula

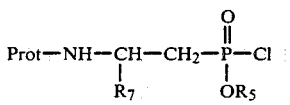
(XVI)

wherein $R_5$ is lower alkyl, benzyl or benzhydryl by treating XV with triethylorthoformate, benzyl bromide, etc., followed by treatment with thionyl chloride or phosphorus pentachloride.

The acid chloride of formula XVI is then coupled with the lactam ester of formula III to yield the intermediate of the formula

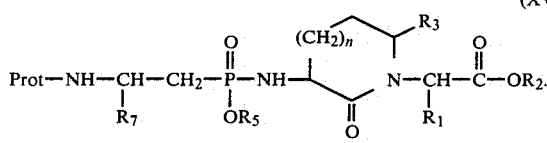
(XVII)

Removal of the protecting group such as by hydrogenation where Prot is benzyloxycarbonyl or by treatment with hydrazine where Prot is phthalidyl followed by reaction with the acid chloride of the formula

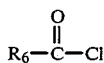
(XVIII)

yields the desired products of formula I.

If $R_1$ is amino or hydroxy substituted lower alkyl then the amino or hydroxy group should be protected during the coupling reaction. Suitable protecting groups include benzyloxycarbonyl, t-butoxycarbonyl, benzyl, benzhydryl, etc. The protecting group is removed by hydrogenation, treatment with acid, or by other known methods following completion of the reaction.

The lactam esters of formula III are prepared according to ring closure processes described in the literature and the Harris et al. applications described above.

Preferred compounds of this invention are those of formula I wherein:

$R_4$ is alkyl of 1 to 10 carbons.

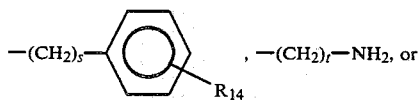

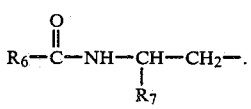

$R_6$ and $R_7$ are selected from lower alkyl of 1 to 4 carbons and

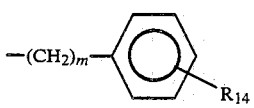, especially wherein $R_6$ is phenyl and $R_7$ is benzyl or phenethyl.

m is zero, one, two, or three.

s is zero or an integer from 1 to 7.

t is an integer from 1 to 8.

$R_{14}$ is hydrogen, methyl, methoxy, methylthio, chloro, bromo, fluoro, or hydroxy.

$R_1$ is hydrogen, lower alkyl of 1 to 4 carbons, or —$(CH_2)_4$—$NH_2$.

$R_3$ is hydrogen, lower alkyl of 1 to 4 carbons, or

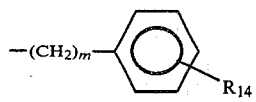

$R_5$ and $R_2$ are independently selected from hydrogen, lower alkyl of 1 to 4 carbons, alkali metal salt, or

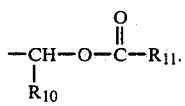

$R_{10}$ is hydrogen, straight or branched chain lower alkyl of 1 to 4 carbons, or cyclohexyl.

$R_{11}$ is straight or branched chain lower alkyl of 1 to 4 carbons, cyclohexyl or phenyl.

Most preferred compounds of this invention are those of formula I wherein: n is one or two.

$R_4$ is alkyl of 1 to 10 carbons or

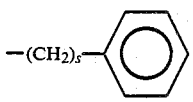

wherein s is zero or an integer from 1 to 7, especially

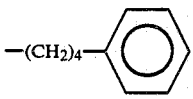.

$R_1$ is hydrogen.
$R_3$ is hydrogen.
$R_5$ and $R_2$ are independently selected from hydrogen, alkali metal salt, and

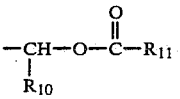

provided that only one of $R_2$ and $R_5$ is

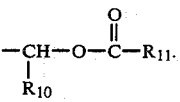.

$R_{10}$ is hydrogen, straight or branched chain lower alkyl of 1 to 4 carbons, or cyclohexyl.

$R_{11}$ is straight or branched chain lower alkyl of 1 to 4 carbons.

The compounds of this invention wherein at least one of $R_5$ or $R_2$ is hydrogen form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The symbol * is used to represent variious asymmetric centers which may be present in the compounds of formula I. Thus, the compounds of this invention can accordingly exist in diastereoisomeric forms or in mixtures thereof. The above described processes can utilize racemates, enantiomers or diasteromers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene-divinylbenzene sulfonic acid cation exchange resin. HP-20 refers to a porous crosslinked polystyrene divinylbenzene polymer resin.

EXAMPLE 1

(S)-3-[[Hydroxy(4-phenylbutyl)phosphinyl]amino]-2-oxo-1-piperidineacetic acid, dilithium salt (a) L-Ornithine, ethyl ester, hydrochloride (1:2)

A heterogeneous mixture of L-ornithine, hydrochloride (7.0 g., 41.5 mmole) and ethanol (200 ml.) at 0° (ice bath) is treated dropwise with thionyl chloride (4.5 ml., 1.5 eq.), then refluxed for 3.5 hours under argon. The ethanol, sulfur dioxide and excess thionyl chloride are removed in vacuo and the resulting crystalline solid is triturated with ether (three times), collected by filtration, and washed with ether to give 9.4 g. of L-ornithine, ethyl ester, hydrochloride (1:2) as a white crystalline solid. A small amount is triturated with hot acetonitrile to give an analytical sample; m.p. 175–176.0. TLC (7:2:1, isopropanol/conc. $NH_4OH$/water) single spot at $R_f=0.50$.

Anal. calc'd. for $C_7H_{16}N_2O_2 \cdot 2HCl$: C, 36.06; H, 7.78; N, 12.02; Cl, 30.41. Found: C, 35.98; H, 7.91; N, 12.02; Cl, 30.29.

(b) (S)-3-Amino-2-oxopiperidine

L-Ornithine, ethyl ester, hydrochloride (1:2) (5.0 g., 21.4 mmole) is treated with 1M sodium ethoxide (42.8 ml., 2.0 eq.) at 25° in an argon atmosphere. After 20 minutes the ethanol is evaporated, the residue is taken up in ethyl acetate and the sodium chloride is filtered off through a Celite bed. The ethyl acetate is evaporated and the resulting off-white solid is triturated with isopropyl ether to give 2.2 g. of (S)-3-amino-2-oxopiperidine as a white crystalline solid. A small portion is recrystallized from isopropyl ether to give fine white needles; m.p. 103°–109° (very hygroscopic).

(c) (S)-3-[[(Phenylmethoxy)carbonyl]amino]-2-oxopiperidine

A heterogeneous mixture of (S)-3-amino-2-oxopiperidine (1.7 g., 14.9 mmole), dry tetrahydrofuran (10 ml.), and diisopropylethylamine (3.6 ml., 1.4 eq.) at 0° (ice bath) under argon is treated with benzyl chloroformate (2.5 ml., 1.2 eq.). After 3 hours, the reaction mixture is diluted with ethyl acetate, and washed successively with water, 5% potassium bisulfate, and brine, dried ($MgSO_4$), and evaporated to give 3.9 g. of a crude white solid. This material is triturated with isopropyl ether to give 3.3 g. of (S)-3-[[(phenylmethoxy)carbonyl]amino]-2-oxopiperidine as a white solid. TLC (ethyl acetate) one spot at $R_f=0.20$. A portion is recrystallized from isopropyl ether to give a white crystalline solid; m.p. 100°–102°.

$[\alpha]_D = -17.6°$ (c=1.0, methanol).

Anal. calc'd. for $C_{13}H_{16}N_2O_3$: C, 62.89; H, 6.49; N, 11.28. Found: C, 62.76; H, 6.47; N, 11.22.

(d) (S)-3-[[(Phenylmethoxy)carbonyl]amino]-2-oxopiperidineacetic acid, ethyl ester A mixture of (S)-3-[[(phenylmethoxy)carbonyl]amino]-2-oxopiperidine (2.9 g., 11.7 mmole), dry tetrahydrofuran (15 ml.), and potassium t-butoxide (1.7 g., 1.3 eq.) at 0° (ice bath) is stirred for 20 minutes under argon and then is treated with ethyl bromoacetate (2.0 ml., 1.5 eq.). The ice bath is removed and the resulting reaction mixture is stirred for 5 hours. The reaction mixture is diluted with ethyl acetate, washed with water and brine, dried (MgSO$_4$), and evaporated. The residue (4.4 g.) is chromatographed on silica (130 g.) eluting with hexane/ethyl acetate (4:3) to give 3.3 g. of (S)-3-[[(phenylmethoxy)carbonyl]amino]-2-oxopiperidineacetic acid, ethyl ester as a colorless oil. TLC (4:3, hexane/ethyl acetate) single spot at R$_f$=0.15.

(e) (S)-3-Amino-2-oxopiperidineacetic acid, ethyl ester (S)-3-[[(Phenylmethoxy)carbonyl]amino]-2-oxopiperidineacetic acid (1.6 g., 4.8 mmole), 10% palladium on carbon catalyst (500 mg.), and methanol (50 ml.) is hydrogenated on the Parr apparatus at 50 psi for 2 hours. The catalyst is removed by filtration (Celite bed) and the methanol evaporated to give 1.0 g. of (S)-3-amino-2-oxopiperidineacetic acid, ethyl ester as an oil.

(f) Ethoxy(4-phenylbutyl)phosphinyl chloride

A mixture of 4-phenylbutyl chloride (8.0 g., 47.5 mmole) and triethylphosphite (15.0 ml., 72 mmole) is heated at reflux (bath temperature 185°) under argon for 41.5 hours. Distillation of the mixture gives 10.8 g. of diethyl(4-phenylbutyl)phosphonate as a colorless liquid; b.p. 152°–154° (1.0 mm of Hg.).

A mixture of diethyl(4-phenylbutyl)phosphonate (0.73 g., 2.6 mmole), benzene (10 ml.) and phosphorus pentachloride (1.0 eq.) is refluxed under argon for 30 minutes. The benzene and phosphorus oxychloride are removed in vacuo to give ethoxy(4-phenylbutyl)phosphinyl chloride.

(g) (S)-3-[[Ethoxy(4-phenylbutyl)phosphinyl]amino]-2-oxo-1-piperidineacetic acid, ethyl ester The ethoxy(4-phenylbutyl)phosphinyl chloride from part (f) is taken up in dry methylene chloride (5 ml.). The 3-amino-2-oxopiperidienacetic acid, ethyl ester from part (e) is taken up in methylene chloride (5 ml.) and added to the above. The resulting solution is cooled to 0° (ice bath) and treated dropwise with triethylamine (1.0 ml., 1.5 eq.) in methylene chloride (2 ml.) for 5 minutes in an argon atmosphere. After 30 minutes, the ice bath is removed and the mixture is stirred for an additional 1 hour. The reaction mixture is then diluted with ethyl acetate, washed successively with saturated sodium bicarbonate, water, and brine, dried (MgSO$_4$), and evaporated. The residue (2.3 g.) is chromatographed on silica (100 g.) eluting with acetone/hexane (2:1) to give 1.1 g. of (S)-3-[[ethoxy(4-phenylbutyl)phosphinyl]amino]-2-oxo-1-piperidineacetic acid, ethyl ester as an oil. TLC (2:1, acetone/hexane) single spot at R$_f$=0.20.

(h) (S)-3-[[Hydroxy(4-phenylbutyl)phosphinyl]amino]-2-oxo-1-piperidineacetic acid, dilithium salt A mixture of the ester product from part (g) (1.1 g., 2.6 mmole), dry methylene chloride (7 ml.), and bromotrimethylsilane (0.6 ml., 1.7 eq.) in an argon atmosphere at room temperature is stirred for 40 hours. The methylene chloride and excess bromotrimethylsilane are removed in vacuo and the residue is taken up in dioxane (10 ml.) and treated with 1N lithium hydroxide (9.1 ml., 3.5 eq.). A white precipitate appears but most of it returns to solution to leave a milky solution. After 2 hours, the dioxane is evaporated. The heterogeneous solution is filtered, and the filtrate is chromatographed on an HP-20 (200 ml.) column eluting with a linear gradient of water→acetonitrile (0→90%). The fractions containing the desired product are combined, evaporated to a small volume, filtered (millipore), and lyophilized to give 480 mg. of (S)-3-[[hydroxy(4-phenylbutyl)phosphinyl]amino]-2-oxo-1-piperidineacetic acid, dilithium salt as a dense white solid; m.p. darkens at 185°. [α]$_D$=−4.9° (c=1.0, water). TLC (7:2:1, isopropanol/NH$_4$OH/water) single spot at R$_f$=0.50.

Anal. calc'd. for C$_{17}$H$_{23}$N$_2$O$_5$PLi$_2$.0.5H$_2$O: C, 52.46; H, 6.21; N, 7.20; P, 7.9. Found: C, 52.38; H, 6.42; N, 7.12; P, 7.8.

EXAMPLE 2

(S)-Hexahydro-3-[[hydroxy(4-phenylbutyl)phosphinyl]amino]-2-oxo-1H-azepine-1-acetic acid, dilithium salt (a) N$^2$-[(1,1-Dimethylethoxy)carbonyl]-N$^6$-[(phenylmethoxy)carbonyl]-L-lysine, methyl ester Cesium carbonate (2.14 g., 6.55 mmole) is added to a mixture of N$^2$-[(1,1-dimethylethoxy)carbonyl]-N$^6$-[(phenylmethoxy)carbonyl]-L-lysine (5.0 g., 13.10 mmole) and 20% aqueous methanol (30 ml.). The solution becomes homogeneous after 5 minutes, the methanol is stripped, and the residual water is removed azeotropically with acetonitrile (twice). The resulting oil is taken up in dry methylene chloride (10 ml.) and treated with methyl iodide (1.6 ml., 2.0 eq.) at 25° in an argon atmosphere. After 4 hours the reaction mixture is taken up in ethyl acetate and washed successively with water, saturated sodium bicarbonate and brine, dried (MgSO$_4$), and evaporated. The residue (4.7 g.) is chromatographed on silica (160 g.) eluting with hexane/ethyl acetate (3:1) to give 4.0 g. of N$^2$-[(1,1-dimethylethoxy)carbonyl]-N$^6$-[(phenylmethoxy)carbonyl]-L-lysine, methyl ester as an oil after evaporation. TLC (hexane/ethyl acetate; 2:1) major spot at R$_f$=0.3.

(b) (S)-3-[[(1,1-Dimethylethoxy)carbonyl]amino]-2-oxohexahydro-1H-azepine

A mixture of N$^2$-[(1,1-dimethylethoxy)carbonyl]-N$^6$-[(phenylmethoxy)carbonyl]-L-lysine, methyl ester (4.0 g., 10.1 mmole), 10% palladium on carbon catalyst (1.0 g.), and methanol (60 ml.) is hydrogenated on the Parr apparatus at 50 psi for 2 hours. The catalyst is removed by filtration (Celite bed) and the methanol evaporated. The resulting oil is taken up in xylene (30 ml.) and refluxed for 18 hours in an argon atmosphere. The xylene is diluted with ethyl acetate and washed successively with 5% potassium bisulfate, saturated sodium bicarbonate and brine, dried (MgSO$_4$), and evaporated to a crystalline solid. The solid is taken up in methylene chloride and chromatographed on silica (60 g.) eluting with ethyl acetate/hexane (1:1) to give 1.5 g. of (S)-3-[[(1,1-dimethylethoxy)carbonyl]amino]-2-oxo-hexahydro-1H-azepine as a white crystalline solid; m.p. 147°–149°; $[\alpha]_D = +4.5°$ (1.0, methanol). TLC (ethyl acetate) shows a single spot at $R_f = 0.50$.

Anal. calc'd. for $C_{11}H_{20}N_2O_3$: C, 57.87; H, 8.83; N, 12.27. Found: C, 58.12; H, 8.63; N, 12.26.

(c)

(S)-3-[[(1,1-Dimethylethoxy)carbonyl]amino]-2-oxo-hexahydro-1H-azepine-1-acetic acid, ethyl ester A mixture of (S)-3-[[(1,1-dimethylethoxy)carbonyl]amino]-2-oxo-hexahydro-1H-azepine (1.4 g., 6.1 mmole), dry tetrahydrofuran (10 ml.), and potassium t-butoxide (0.9 g., 1.3 eq.) is stirred under argon at room temperature for 5 minutes, then treated with ethyl bromoacetate (1.1 ml., 1.7 eq.). After 1 hour, the reaction mixture is diluted with ethyl acetate and washed successively with saturated sodium bicarbonate, 5% potassium bisulfate, and brine, dried (MgSO₄), and evaporated. The orange residue (2.4 g.) is chromatographed on silica (65 g.) eluting with ethyl acetate/hexane (3:1) to give 1.65 g. of (S)-3-[[(1,1-dimethylethoxy)carbonyl]amino]-2-oxo-hexahydro-1H-azepine-1-acetic acid, ethyl ester as a colorless oil. TLC (hexane/ethyl acetate; 1:1) single spot at $R_f = 0.4$.

(d) (S)-3-Amino-2-oxo-hexahydro-1H-azepine-1-acetic acid, ethyl ester, monohydrochloride A mixture of (S)-3-[[(1,1-dimethylethoxy)carbonyl]amino]-2-oxo-hexahydro-1H-azepine-1-acetic acid, ethyl ester (1.6 g., 5.0 mmole) and ethyl acetate (5 ml.) at 0° (ice bath) is treated with cold saturated hydrochloric acid/ethyl acetate (40 ml.). After stirring for 45 minutes at 0°, nitrogen is passed through the solution to remove excess hydrochloric acid. The ethyl acetate is evaporated and the resulting oil is triturated with ether (3 times) to give 1.1 g. of (S)-3-amino-2-oxo-hexahydro-1H-azepine-1-acetic acid, ethyl ester, monohydrochloride as a very hygroscopic white crystalline solid after drying in vacuo over phosphorus pentoxide. TLC (methylene chloride/acetic acid/methanol; 8:1:1) major spot at $R_f = 0.32$.

(e)

(S)-Hexahydro-3-[[ethoxy(4-phenylbutyl)phosphinyl]amino]-2-oxo-1H-azepine-1-acetic acid, ethyl ester A mixture of ethoxy(4-phenylbutyl)phosphinyl chloride [4.4 mmole; prepared as set forth in Example 1(f)], dry tetrahydrofuran (10 ml.), and 3-amino-2-oxo-hexahydro-1H-azepine-1-acetic acid, ethyl ester, monohydrochloride (1.0 g., 4.0 mmole) at 0° (ice bath) in an argon atmosphere is treated dropwise with triethylamine (1.7 ml., 3.0 eq.) in tetrahydrofuran (5 ml.) over 2 minutes. After 20 minutes, the ice bath is removed and the reaction mixture is stirred for an additional 1.5 hours. The reaction mixture is diluted with ethyl acetate and washed successively with saturated sodium bicarbonate, 5% potassium bisulfate, and brine, dried (MgSO₄) and evaporated. The residue (2.1 g.) is chromatographed on silica (65 g.) eluting with ethyl acetate then acetone to give 1.0 g. of (S)-hexahydro-3-[[ethoxy(4-phenylbutyl)phosphinyl]amino]-2-oxo-1H-azepine-1-acetic acid, ethyl ester as an oil after evaporation. TLC (ethyl acetate) single spot at $R_f = 0.1$.

(f)

(S)-Hexahydro-3-[[hydroxy(4-phenylbutyl)phosphinyl]amino]-2-oxo-1H-azepine-1-acetic acid, dilithium salt A mixture of the diester product from part (e) (1.0 g., 2.3 mmole), methylene chloride (3 ml.), and bromotrimethylsilane (0.9 ml., 3.0 eq.) is stirred at 25° under argon for 16 hours. The methylene chloride and excess bromotrimethylsilane are removed in vacuo and the residue is taken up in acetonitrile (7 ml.) and 1N lithium hydroxide (7 ml., 3.0 eq.). After 3 hours the acetonitrile is evaporated, the aqueous solution is filtered, and chromatographed on an HP-20 (200 ml.) column eluting with a linear gradient water-acetonitrile (0→90% acetonitrile). The fractions containing the desired product are combined, evaporated to a small volume, filtered (millipore) and lyophilized to give 680 mg. of (S)-hexahydro-3-[[hydroxy(4-phenylbutyl)phosphinyl]amino]-2-oxo-1H-azepine-1-acetic acid, dilithium salt as a fluffy white solid; m.p. greater than 250°; $[\alpha]_D = +14.8°$ (c = 0.5, water). TLC (isopropanol/conc. NH₄OH/water; 7:2:1) single spot at $R_f = 0.72$.

Anal. Calc'd. for $C_{18}H_{25}N_2O_5PLi_2 \cdot 1.5H_2O$: C, 51.32; H, 6.69; N, 6.65; P, 7.3. Found: C, 51.20; H, 6.33; N, 6.62; P, 7.3.

EXAMPLES 3–22

Following the procedures of Examples 1 and 2, the lactam ester shown below in Col. I is reacted with the alkoxy(alkyl)phosphinyl chloride shown in Col. II to give the ester product shown in Col. III. The $R_2$ and $R_5$ ester groups can be removed to give the corresponding diacid which can then be converted to a salt or in the case of Examples 20 to 22 only the $R_5$ ester group would be removed. The $R_1$ protecting group shown in Examples 6 and 10 would be removed as the last step of the synthesis.

Col. I

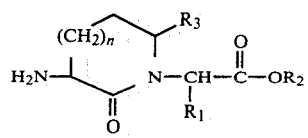

Col. II

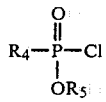

Col. III

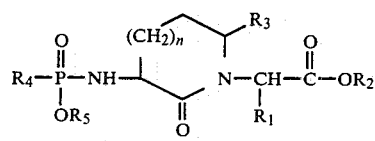

| Example | n | $R_3$ | $R_1$ | $R_2$ | $R_4$ | $R_5$ |
|---|---|---|---|---|---|---|
| 3 | 1 | —H | —H | —$C_2H_5$ | Ph—$(CH_2)_4$— | —$C_2H_5$ |
| 4 | 2 | —Ph | —$CH_3$ | —$C_2H_5$ | Ph—$(CH_2)_6$— | —$C_2H_5$ |
| 5 | 1 | —$CH_3$ | —H | —$CH_2$Ph | Ph—$(CH_2)_2$— | —$CH_2$Ph |
| 6 | 2 | —$C_2H_5$ | —$(CH_2)_4$NHCOCH$_2$Ph | —$C_2H_5$ | $H_3C$—$(CH_2)_7$— | —$C_2H_5$ |
| 7 | 1 | —$CH_2$-C$_6$H$_4$-$CH_3$ | —H | —$C_2H_5$ | $H_3C$—$(CH_2)_3$— | —$C_2H_5$ |
| 8 | 2 | —$(CH_2)_2$Ph | —$CF_3$ | —$C_2H_5$ | thienyl-$(CH_2)_4$— | —$C_2H_5$ |
| 9 | 1 | —$CH_2$-cyclohexyl | —$C_2H_5$ | —$C_2H_5$ | furyl— | —$C_2H_5$ |
| 10 | 2 | cyclopentyl | —$CH_2OCH_2$Ph | —$C_2H_5$ | pyridyl-$CH_2$— | —$C_2H_5$ |
| 11 | 1 | —$C(CH_3)_3$ | —H | —$C_2H_5$ | F-C$_6$H$_4$-$CH_2$— | —$C_2H_5$ |
| 12 | 2 | —H | —H | —$C_2H_5$ | Cl$_2$-C$_6$H$_3$-$(CH_2)_2$— | —$C_2H_5$ |
| 13 | 1 | —H | —H | —$C_2H_5$ | $H_3CO$-C$_6$H$_4$-$(CH_2)_4$— | —$C_2H_5$ |
| 14 | 3 | —H | —H | —$C_2H_5$ | Ph—$(CH_2)_4$— | —$C_2H_5$ |

-continued

Col. I

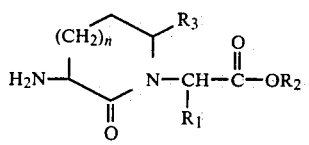

Col. II

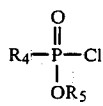

Col. III

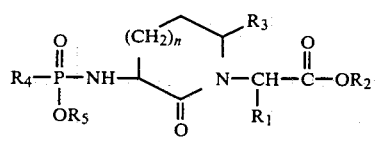

| Example | n | R₃ | R₁ | R₂ | R₄ | R₅ |
|---|---|---|---|---|---|---|
| 15 | 4 | —H | —H | —C₂H₅ | phenyl—(CH₂)₄— | —C₂H₅ |
| 16 | 1 | —H | —H | —C₂H₅ | furyl—CH₂— | —C₂H₅ |
| 17 | 2 | —CH₃ | —CH₃ | —C₂H₅ | phenyl— | —C₂H₅ |
| 18 | 1 | —H | —CH₃ | —C₂H₅ | H₃C—phenyl—(CH₂)₃— | —C₂H₅ |
| 19 | 2 | —H | —H | —C₂H₅ | cyclohexyl—(CH₂)₄— | —C₂H₅ |
| 20 | 1 | —phenyl | —H | —CH—O—C(O)—C₂H₅ (with cyclohexyl) | phenyl—(CH₂)₄— | —C₂H₅ |
| 21 | 2 | —H | —H | —CH(CH(CH₃)₂)—O—C(O)—C₂H₅ | phenyl—(CH₂)₄— | —C₂H₅ |
| 22 | 3 | —H | —CH₃ | —CH(C₂H₅)—O—C(O)—phenyl | phenyl—(CH₂)₂— | —C₂H₅ |

EXAMPLE 23

(S)-3-[[(6-Aminohexyl)hydroxyphosphinyl]amino]-2-oxo-1-piperidineacetic acid, dilithium salt (a) N-(6-Bromohexyl)phthalimide A mixture of crystalline 6-aminohexanol (11.7 g., 0.1 mole) and phthalic anhydride (14.8 g., 0.1 mole) is heated at 170° for 1.5 hours in an argon atmosphere. The evolved water is then removed with heat and argon flow. The reaction mixture is cooled to 100° and phosphorus tribromide (7.2 ml., 0.086 mole) is added in portions via gas tight syringe to the reaction mixture. A vigorous reaction occurs with each addition. After addition is complete, the reaction mixture is heated at 100° for an additional 30 minutes. The cooled reaction mixture is diluted with ethanol (20 ml.) then poured over ice-water and refrigerated overnight. A yellow solid is filtered and washed several times with cold water until the filtrate is nearly neutral. The crude solid is recrystallized from ethanol to give 21.0 g. of N-(6-bromohexyl)phthalimide as a pale yellow solid; m.p. 54°–55°. TLC (hexane-ethyl acetate; 1:1) shows a major spot at $R_f=0.8$.

(b) (6-Phthalimidohexyl)phosphonic acid, diethyl ester

A mixture of N-(6-bromohexyl)phthalimide (5.5 g., 17.7 mmole) and triethylphosphite (10.0 ml., 58.4 mmole) is refluxed (bath temperature 160°–165°) under argon for 16 hours. The volatiles are removed by distillation at 100° (bath temperature), 0.5 mm. of Hg to leave a pale yellow viscous oil. The crude product is purified by flash chromatography on silica gel (100 g.) eluting with acetone-hexane (1:2) to give 6.00 g. of (6-phthalimidohexyl)phosphonic acid, diethyl ester as a colorless viscous oil. TLC (acetone-hexane; 1:1) shows a single spot at $R_f-0.40$.

(c) Ethoxy(6-phthalimidohexyl)phosphinyl chloride

A mixture of (6-phthalimidohexyl)phosphonic acid, diethyl ester, benzene, and phosphorus pentachloride is refluxed according to the procedure of Example 1(f) to give ethoxy(6-phthalimidohexyl)phosphinyl chloride.

(d) (S)-3-[[Ethoxy(6-phthalimidohexyl)phosphinyl]amino]-2-oxo-1-piperidineacetic acid, ethyl ester Ethoxy(6-phthalimidohexyl)phosphinyl chloride and (S)-3-amino-2-oxopiperidineacetic acid, ethyl ester are reacted according to the procedure of Example 1(g) to give (S)-3-[[ethoxy(6-phthalimidohexyl)phosphinyl]amino]-2-oxo-1-piperidineacetic acid, ethyl ester.

(e) (S)-3-[[(6-Aminohexyl)ethoxyphosphinyl]amino]-2-oxo-1-piperidineacetic acid, ethyl ester A solution of (S)-3-[[ethoxy(6-phthalimidohexyl)phosphinyl]amino]-2-oxo-1-piperidineacetic acid, ethyl ester in dioxane is treated with hydrazine hydrate and stirred at room temperature under argon. After the reaction is completed, the mixture is diluted with toluene and the solvents decanted. The residue is triturated with methylene chloride and filtered. The combined filtrate is evaporated to dryness to give (S)-3-[[(6-aminohexyl)ethoxyphosphinyl]amino]-2-oxo-1-piperidineacetic acid, ethyl ester.

(f) (S)-3-[[(6-Aminohexyl)hydroxyphosphinyl]amino]-2-oxo-1-piperidineacetic acid, dilithium salt The diethyl ester product from part (e) is treated with bromotrimethylsilane in methylene chloride and the residue is taken up in acetonitrile and treated with 1N lithium hydroxide according to the procedure of Example 1(h). Work-up of the product according to the procedure of Example 1(h) gives (S)-3-[[(6-aminohexyl)hydroxyphosphinyl]amino]-2-oxo-1-piperidineacetic acid, dilithium salt.

EXAMPLES 24–27

Following the procedure of Example 23 but employing the aminoalcohol listed in Col. I one obtains the product listed in Col. II.

| Ex. | Col. I | Col. II |
|---|---|---|
| 24 | 3-aminopropanol | (S)—3-[[(3-Aminopropyl)-hydroxyphosphinyl]amino]-2-oxo-1-piperidineacetic acid, dilithium salt |
| 25 | 2-aminoethanol | (S)—3-[[(2-Aminoethyl)-hydroxyphosphinyl]amino]-2-oxo-1-piperidineacetic acid, dilithium salt |
| 26 | 4-aminobutanol | (S)—3-[[(4-Aminobutyl)-hydroxyphosphinyl]amino]-2-oxo-1-piperidineacetic acid, dilithium salt |
| 27 | 8-aminooctanol | (S)—3-[[(8-Aminooctyl)-hydroxyphosphinyl]amino]-2-oxo-1-piperidineacetic acid, dilithium salt |

Similarly, by employing the lactam esters of Examples 2 to 22 within the procedure of Examples 23 to 27, other compounds within the scope of the invention are obtained.

EXAMPLE 28

(S)-3-[[[2-(Benzoylamino)-3-phenylpropyl]hydroxyphosphinyl]amino]-2-oxo-1-piperidineacetic acid, dilithium salt (a) 4-Methylbenzenesulfonic acid, 2-[[(4-methylphenyl)sulfonyl]amino]-3-phenylpropyl ester A solution of d,l-phenylalaninol, hydrochloride (9.4 g., 50.1 mmole) in dry pyridine (35 ml.) at 0° (ice bath) is treated with p-toluenesulfonyl chloride (19.4 g., 102 mmole) in small portions over a 15 minute period. The mixture is allowed to come to room temperature and stirred overnight. The mixture is evaporated to dryness and the residue partitioned between ethyl acetate and 5% potassium bisulfate. The ethyl acetate layer is washed successively with 5% potassium bisulfate, saturated sodium bicarbonate and saturated sodium chloride, dried (Na$_2$SO$_4$), and evaporated. The dark residue is filtered through a pad of silica gel eluting with methylene chloride then methylene chloride-ethyl acetate (1:1). Evaporation of the solvents and trituration of the residue with ether gives 13.93 g. of 4-methylbenzenesulfonic acid, 2-[[(4-methylphenyl)sulfonyl]amino]-3-phenylpropyl ester as white crystals; m.p. 95°–96°; TLC (ethyl acetate/hexane; 1:2) spot at $R_f=0.39$. A sample is recrystallized from diisopropyl ether; m.p. 96°–98°.

(b) [2-[[(4-Methylphenyl)sulfonyl]amino]-3-phenylpropyl]phosphonic acid, diethyl ester A solution of diethylphosphite (7.3 g., 52.9 mmole) in dry tetrahydrofuran (100 ml.) is treated with sodium hydride 50% oil dispersion (2.20 g., 45.8 mmole) in small portions under argon. The mixture is then refluxed for 30 minutes, cooled to room temperature, and treated with 4-methylbenzenesulfonic acid, 2-[[(4-methylphenyl)sulfonyl]amino]-3-phenylpropyl ester (6.9 g., 15 mmole). After 15 minutes, a white solid separates; additional tetrahydrofuran (75 ml.) is added and stirring continued overnight. After stirring at room temperature overnight, the mixture is refluxed for one hour, cooled and partitioned between ethyl acetate (75 ml.) and 5% potassium bisulfate (50 ml.). The ethyl acetate phase is washed successively with 5% potassium bisulfate, saturated sodium bicarbonate and saturated sodium chloride, dried (Na$_2$SO$_4$), and evaporated. The residue is triturated with hexane to give 5.9 g. of [2-[[(4-methylphenyl)sulfonyl]amino]-3-phenylpropyl]phosphonic acid, diethyl ester as an off-white solid; m.p. 86°–89°; TLC (ethyl acetate) spot at $R_f=0.48$. A sample is recrystallized from diisopropyl ether; m.p. 94°–95°.

(c) (2-Amino-3-phenylpropyl)phosphonic acid

A mixture of [2-[[(4-methylphenyl)sulfonyl]amino]-3-phenylpropyl]phosphonic acid, diethyl ester (5.9 g., 13.9 mmole), phenol (8.0 g., 85.1 mmole), and 48% aqueous hydrobromic acid (50 ml.) is refluxed for 5.5 hours. The cooled mixture is diluted with water (50 ml.) and washed with ethyl acetate ($2 \times 50$ ml.). The aqueous phase is evaporated to dryness, taken up in water (30 ml.) and evaporated again. This is repeated twice more. Finally, the residue is taken up in water and applied to an AG 50 W-X2 (H+ form) column (60 ml. bed volume) and eluted first with water then with 5% pyridine-water. The fractions containing the desired product are combined and evaporated to dryness. The solid residue is triturated with acetonitrile to give 2.55 g. of (2-amino-3-phenylpropyl)phosphonic acid as an off-white crystalline solid; m.p. 347° (dec.); TLC (isopropanol/conc. NH$_4$OH/water; 7:2:1) spot at $R_f=0.27$.

(d) (2-Phthalimido-3-phenylpropyl)phosphonic acid

A mixture of (2-amino-3-phenylpropyl)phosphonic acid (2.0 g., 9.3 mmole) and phthalic anhydride (1.55 g., 10.5 mmole) is fused in a flask under argon at 195°–200° (bath temperature) for 1.5 hours. The glassy dark residue is refluxed with ethyl acetate (25 ml.) until the glassy residue dissolves and a fluffy crystalline solid separates. The cooled mixture is diluted with diethyl ether (25 ml.) and filtered. The solid is washed thoroughly with diethyl ether and dried to give 2.87 g. of (2-phthalimido-3-phenylpropyl)phosphonic acid as an off-white crystalline solid; m.p. 127°–130°. A sample is crystallized from ethyl acetate; m.p. 129°–131°. TLC (isopropanol/conc. NH$_4$OH/water; 7:2:1) spot at $R_f=0.33$.

(e) (S)-3-[[[2-Phthalimido-3-phenylpropyl]ethoxyphosphinyl]amino]-2-oxo-1-piperidineacetic acid, ethyl ester A suspension of (2-phthalimido-3-phenylpropyl)phosphonic acid in dry benzene is treated with phosphorus pentachloride and stirred at room temperature under argon for an hour. The mixture is then refluxed for 15 minutes, cooled and evaporated to dryness at room temperature (0.5 mm. of Hg). The residue is taken up in dry methylene chloride and reacted successively with a mixture of ethanol (1 eq.) and triethylamine (1 eq.) in methylene chloride and (S)-3-amino-2-oxopiperidineacetic acid, ethyl ester according to the procedure of Example 1(g). Work up of the reaction mixture according to the procedure of Example 1(g) yields (S)-3-[[[2-phthalimido-3-phenylpropyl]ethoxyphosphinyl]amino]-2-oxo-1-piperidineacetic acid, ethyl ester.

(f) (S)-3-[[[2-(Benzoylamino)-3-phenylpropyl]ethoxyphosphinyl]amino]-2-oxo-1-piperidineacetic acid, ethyl ester A solution of (S)-3-[[[2-phthalimido-3-phenylpropyl]ethoxyphosphinyl]amino]-2-oxo-1-piperidineacetic acid, ethyl ester in dioxane is treated with hydrazine hydrate and stirred for 24 hours at room temperature. The mixture is then partitioned between ethyl acetate-water and the ethyl acetate phase is washed with water and saturated sodium chloride, dried (Na$_2$SO$_4$), and evaporated. The residue is taken up in dry toluene and refluxed for one hour. The mixture is filtered, treated with triethylamine and benzoyl chloride and stirred at room temperature for 30 minutes. The mixture is diluted with ethyl acetate, washed successively with 5% potassium bisulfate, saturated sodium bicarbonate, and saturated sodium chloride, dried (Na$_2$SO$_4$), and evaporated. The residue is chromatographed on silica gel to give (S)-3-[[[2-(benzoylamino)-3-phenylpropyl]ethoxyphosphinyl]amino]-2-oxo-1-piperidineacetic acid, ethyl ester.

(g) (S)-3-[[[2-(Benzoylamino)-3-phenylpropyl]hydroxyphosphinyl]amino]-2-oxo-1-piperidineacetic acid, dilithium salt The diethyl ester product from part (f) is treated with bromotrimethylsilane in methylene chloride and the residue is taken up in acetonitrile and treated with 1N lithium hydroxide according to the procedure of Example 1(h). Work up of the product according to the procedure of Example 1(h) gives (S)-3-[[[2-(benzoylamino)-3-phenylpropyl]hydroxyphosphinyl]amino]-2-oxo-1-piperidineacetic acid, dilithium salt.

EXAMPLES 29–38

Following the procedure of Example 28 but employing the protected amine shown in Col. I and the phosphonic diester shown in Col. II, one obtains, after removal of the tosyl protecting group and reaction with phthalic anhydride, the phosphonic acid shown in Col. III. The acid of Col. III is then converted to the phosphonic acid ester chloride shown in Col. IV which is then coupled with the lactam ester shown in Col. V to yield the intermediate shown in Col. VI. Removal of the phthalidyl group and reaction with the acid chloride shown in Col. VII yields the ester product shown in Col. VIII. The $R_2$ and $R_5$ ester groups can be removed to give the corresponding diacid which can then be converted to a salt or in the case of Example 38 only the $R_5$ ester group would be removed. The $R_1$ protecting group shown in Example 33 would be removed ad the last step of the synthesis.

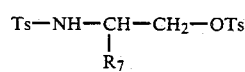 Col. I

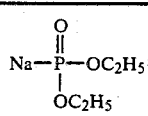 Col. II

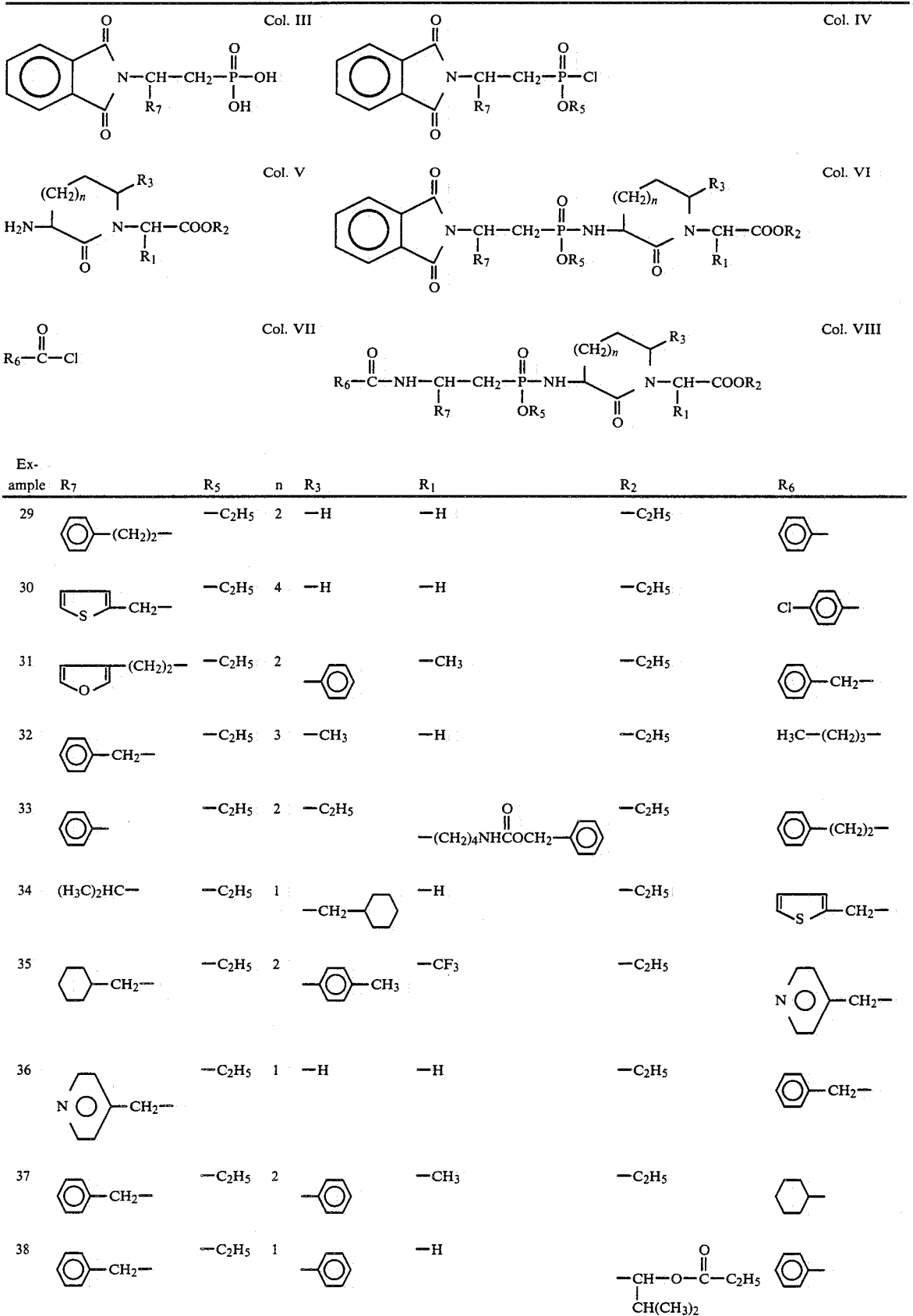

EXAMPLE 39

(S)-Hexahydro-3-[[[2-methyl-1-(1-oxopropoxy)propoxy](4-phenylbutyl)phosphinyl]amino]-2-oxo-1H-azepine-1-acetic acid, monolithium salt (a) (S)-3-Amino-2-oxo-hexahydro-1H-azepine-1-acetic acid, phenylmethyl ester Following the procedure of Example 2(c) but employing bromoacetic acid, phenylmethyl ester for the ethyl bromoacetate, one obtains (S)-3-[[(1,1-dimethylethoxy)carbonyl]amino]-2-oxohexahydro-1H-azepine-1-acetic acid, phenylmethyl ester.

Treatment of this phenylmethyl ester product with trifluoroacetic acid gives (S)-3-amino-2-oxohexahydro-1H-azepine-1-acetic acid, phenylmethyl ester.

(b) (S)-Hexahydro-3-[[ethoxy(4-phenylbutyl)phosphinyl]amino]-2-oxo-1H-azepine-1-acetic acid, phenylmethyl ester Ethoxy(4-phenylbutyl)phosphinyl chloride is reacted with (S)-3-amino-2-oxohexahydro-1H-azepine-1-acetic acid, phenylmethyl ester according to the procedure of Example 2(e) to give (S)-hexahydro-3-[[ethoxy(4-phenylbutyl)phosphinyl]amino]-2-oxo-1H-azepine-1-acetic acid, phenylmethyl ester.

(c) (S)-Hexahydro-3-[[[2-methyl-1-(1-oxopropoxy)propoxy](4-phenylbutyl)phosphinyl]amino]-2-oxo-1H-azepine-1-acetic acid, phenylmethyl ester A mixture of the diester product from part (b) and bis(trimethylsilyl)acetamide in methylene chloride is stirred at ambient temperature for several hours. After concentration in vacuo at 30°, methylene chloride is added followed by bromotrimethylsilane. The mixture is stirred at room temperature for several hours and concentrated in vacuo overnight. The residue is dissolved in methylene chloride and treated with triethylamine and water and again concentrated in vacuo. The residue is taken up in chloroform and treated with triethylamine, 1-chloroisobutyl propanoate, sodium chloride, and tetrabutylammonium iodide. The mixture is stirred at reflux temperature overnight. The reaction mixture is then concentrated in vacuo and ether is added to the residue. The water soluble solids separating from solution are filtered off and the ethereal filtrate is washed with water, 2% sodium thiosulfate, and brine, dried (MgSO$_4$), and concentrated in vacuo to give (S)-hexahydro-3-[[[2-methyl-1-(1-oxopropoxy)propoxy](4-phenylbutyl)phosphinyl]amino]-2-oxo-1H-azepine-1-acetic acid, phenylmethyl ester.

(d) (S)-Hexahydro-3-[[[2-methyl-1-(1-oxopropoxy)propoxy](4-phenylbutyl)phosphinyl]amino]-2-oxo-1H-azepine-1-acetic acid, monolithium salt The diester product from part (c) is hydrogenated by treating with palladium on carbon catalyst (10%) in aqueous methanol in a Parr apparatus at 50 psi for several hours. The reaction mixture is filtered and concentrated. The residue is dissolved in ethyl acetate, treated with triethylamine, and concentrated in vacuo. The residue is dissolved in water and applied to an AG50X-8(Li+) column eluting with water. Fractions containing the desired product are combined and lyophilized. The lyophilate is chromatographed on an HP-20 column eluting with a linear gradient of acetonitrile/water (0→90%). Fractions containing the desired product are combined, concentrated in vacuo and the residue is dissolved in water, filtered, and lyophilized to give (S)-hexahydro-3-[[[2-methyl-1-(1-oxopropoxy)propoxy](4-phenylbutyl)phosphinyl]amino]-2-oxo-1H-azepine-1-acetic acid, monolithium salt.

EXAMPLES 40-45

Following the procedure of Example 39 but substituting for the 1-chloroisobutyl propanoate the alkylating agents listed below in Col. I, the products listed in Col. II are obtained.

| Example | Col. I | Col. II |
|---|---|---|
| 40 | Cl—CH(cyclohexyl)—O—C(=O)—C$_2$H$_5$ | (S)—Hexahydro-3-[[[cyclohexyl(1-oxopropoxy)methoxy](4-phenylbutyl)phosphinyl]amino]-2-oxo-1H—azepine-1-acetic acid, monolithium salt |
| 41 | Cl—CH(CH$_3$)—O—C(=O)—C$_2$H$_5$ | (S)—Hexahydro-3-[[[1-(1-oxopropoxy)ethoxy](4-phenylbutyl)phosphinyl]amino]-2-oxo-1H—azepine-1-acetic acid, monolithium salt |
| 42 | Cl—CH$_2$—O—C(=O)—C(CH$_3$)$_3$ | (S)—Hexahydro-3-[[[(2,2-dimethyl-1-oxypropoxy)methoxy](4-phenylbutyl)phosphinyl]amino]-2-oxo-1H—azepine-acetic acid, monolithium salt |
| 43 | Cl—CH(CH(CH$_3$)$_2$)—O—C(=O)—(CH$_2$)$_2$CH$_3$ | (S)—Hexahydro-3-[[[2-methyl-1-(1-oxobutoxy)propoxy[(4-phenylbutyl)phosphinyl]amino]-2-oxo-1H—azepine-1-acetic acid, monolithium salt |
| 44 | Cl—CH$_2$—O—C(=O)—C$_6$H$_5$ | (S)—Hexahydro-3-[[[(phenylcarbonyloxy)methoxy]-(4-phenylbutyl)phosphinyl]amino]-2-oxo-1H—azepine-1-acetic acid, monolithium salt |
| 45 | Cl—CH$_2$—O—C(=O)—OC$_2$H$_5$ | (S)—Hexahydro-3-[[[(ethoxycarbonyloxy)methoxy]-(4-phenylbutyl)phosphinyl]amino]-2-oxo-1H—azepine-1-acetic acid, monolithium salt |

Similarly, the alkylating agents of Examples 39 to 45 can be employed with the ester products of Examples 1 and 3 to 38 to yield other compounds within the scope of this invention.

EXAMPLE 46

(S)-3-[[Hydroxy(4-phenylbutyl)phosphinyl]amino]-2-oxo-1-piperidineacetic acid, disodium salt Following the procedure of Example 1 but substituting sodium hydroxide for the lithium hydroxide in part (h), one obtains (S)-3-[[hydroxy(4-phenylbutyl)phosphinyl]amino]-2-oxo-1-piperidineacetic acid, disodium salt.

This procedure can be employed in Examples 2–45 to give the corresponding mono or disodium salt. In a similar manner, the corresponding mono or dipotassium salt can be obtained.

EXAMPLE 47

1000 tablets each containing the following ingredients:

| | |
|---|---|
| (S)—3-[[Hydroxy(4-phenylbutyl)phosphinyl]amino]-2-oxo-1-piperidineacetic acid, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (S)-3-[[hydroxy(4-phenylbutyl)phosphinyl]amino]-2-oxo-1-piperidineacetic acid, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 45 can be prepared.

EXAMPLE 48

1000 tablets each containing the following ingredients:

| | |
|---|---|
| (S)—Hexahydro-3-[[hydroxy(4-phenylbutyl)phosphinyl]amino]-2-oxo-1H—azepine-1-acetic acid, disodium salt | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the (S)-hexahydro-3-[[hydroxy(4-phenylbutyl)phosphinyl]amino]-2-oxo-1H-azepine-1-acetic acid, disodium salt, lactose and Avicel and then blending with the corn starch. Magnesium stearate is added and the dry mixture is compressed in a tablet press to form 1000 tablets each containing 50 mg. of active ingredient. The tablets are coated with a solution of Methocel E 15 (methyl cellulose) including as a color a lake containing yellow #6.

In a similar manner, tablets containing 50 mg. of the product of any Examples 1 and 3 to 45 can be prepared.

EXAMPLE 49

Two piece #1 gelatin capsules each containing 100 mg. of (S)-3-[[[2-(benzoylamino)-3-phenylpropyl]hydroxyphosphinyl]amino]-2-oxo-1-piperidineacetic acid, disodium salt are filled with a mixture of the following ingredients:

| | |
|---|---|
| (S)—3-[[[2-(Benzoylamino)-3-phenylpropyl]hydroxyphosphinyl]amino]-2-oxo-1-piperidineacetic acid, disodium salt | 100 mg. |
| Magnesium stearate | 7 mg. |
| Lactose | 193 mg. |
| | 300 mg. |

In a similar manner, capsules containing 100 mg. of the product of any of Examples 1 to 27 and 29 to 46 can be prepared.

EXAMPLE 50

An injectable solution is prepared as follows:

| | |
|---|---|
| (S)—3-[[Hydroxy(4-phenylbutyl)phosphinyl]amino]-2-oxo-1-piperidineacetic acid, disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 2 to 46.

EXAMPLE 51

1000 tablets each containing the following ingredients:

| | |
|---|---|
| (S)—Hexahydro-3-[[hydroxy(4-phenylbutyl)phosphinyl]amino]-2-oxo-1H—azepine-1-acetic acid, disodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the (S)-hexahydro-3-[[hydroxy(4-phenylbutyl)phosphinyl]amino]-2-oxo-1H-azepine-1-acetic acid, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 and 3 to 46.

What is claimed is:

1. A compound of the formula wherein

R₁ is hydrogen, lower alkyl, amino substituted lower alkyl, hydroxy substituted lower alkyl, or halo substituted lower alkyl;

n is 3 or 4;

R₃ is hydrogen, lower alkyl, —(CH₂)$_m$-cycloalkyl, or m is zero or an integer from 1 to 4;

R₁₄ is hydrogen, lower alkyl of 1 to 4 carbons, lower alkoxy of 1 to 4 carbons, lower alkylthio of 1 to 4 carbons, halo, trifluoromethyl, or hydroxy;

p is an integer from 1 to 3 provided that p is more than one only if R₁₄ is hydrogen, methyl, methoxy, chloro, or fluoro;

R₄ is alkyl of 1 to 10 carbons, s is zero or an integer from 1 to 7;

t is an integer from 1 to 8;

R₆ and R₇ are independently selected from the group consisting of lower alkyl, halo substituted lower alkyl, —(CH₂)$_m$-cycloalkyl, R₅ and R₂ are independently selected from the group consisting of hydrogen, lower alkyl, benzyl, benzhydryl, physiologically acceptable salt forming ion, and $$-\underset{\underset{R_{10}}{|}}{CH}-O-\overset{\overset{O}{\|}}{C}-R_{11};$$

R₁₀ is hydrogen, lower alkyl, cycloalkyl, or phenyl; and

R₁₁ is hydrogen, lower alkyl, lower alkoxy, cycloalkyl, phenyl, benzyl, or phenethyl.

2. A compound of claim 1 wherein:

R₄ is alkyl of 1 to 10 carbons,

R₆ and R₇ are independently selected from the group consisting of lower alkyl of 1 to 4 carbons and s is zero or an integer from 1 to 7;

t is an integer from 1 to 8;

m is zero, one, two or three;

R₁₄ is hydrogen, methyl, methoxy, methylthio, chloro, bromo, fluoro, or hydroxy;

R₁ is hydrogen, lower alkyl of 1 to 4 carbons, or —(CH₂)₄—NH₂;

R₃ is hydrogen, lower alkyl of 1 to 4 carbons or

R₅ and R₂ are independently selected from the group consisting of hydrogen, lower alkyl of 1 to 4 carbons, alkali metal salt, and $$-\underset{\underset{R_{10}}{|}}{CH}-O-\overset{\overset{O}{\|}}{C}-R_{11};$$

R₁₀ is hydrogen, straight or branched chain lower alkyl of 1 to 4 carbons, or cyclohexyl; and R₁₁ is straight or branched chain lower alkyl of 1 to 4 carbons, cyclohexyl or phenyl.

3. A compound of claim 2 wherein

R₄ is alkyl of 1 to 10 carbons or s is zero or an integer from 1 to 7;

$R_1$ is hydrogen;

$R_3$ is hydrogen;

$R_5$ and $R_2$ are independently selected from the group consisting of hydrogen, alkali metal salt, and

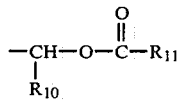

provided that only one of $R_2$ and $R_5$ is

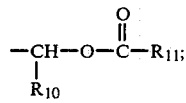

$R_{10}$ is hydrogen, straight or branched chain lower alkyl of 1 to 4 carbons, or cyclohexyl; and $R_{11}$ is straight or branched chain lower alkyl of 1 to 4 carbons.

4. A composition useful for treating hypertension comprising a pharmaceutically acceptable carrier and an effective amount of a hypotensive agent or pharmaceutically acceptable salt thereof of the formula

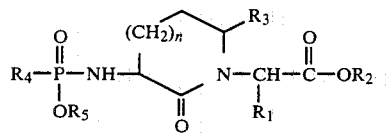

wherein n, $R_1$, $R_2$, $R_3$, $R_4$ and $R_5$ are as defined in claim 1.

5. A method of treating hypertension in a mammalian specie which comprises administering a hypotensively effective amount of the composition of claim 4.

6. A compound of claim 3 wherein n is three.

7. A compound of claim 6 wherein $R_4$ is

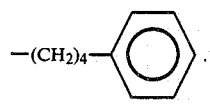

8. A compound of claim 3 wherein n is four.

9. A compound of claim 8 wherein $R_4$ is

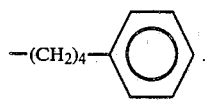

* * * * *